(12) United States Patent
Hertle

(10) Patent No.: US 9,095,505 B2
(45) Date of Patent: Aug. 4, 2015

(54) PYRETHROIDS FOR TREATMENT OF OCULAR MOVEMENT DISORDERS

(71) Applicant: Richard W. Hertle, Hudson, OH (US)

(72) Inventor: Richard W. Hertle, Hudson, OH (US)

(73) Assignee: RBG Group, LTD., Akron, OH (US)

( * ) Notice: Subject to any disclaimer, the term of this patent is extended or adjusted under 35 U.S.C. 154(b) by 3 days.

(21) Appl. No.: 14/075,292

(22) Filed: Nov. 8, 2013

(65) Prior Publication Data

US 2015/0133545 A1   May 14, 2015

(51) Int. Cl.
*A61K 31/275* (2006.01)
*A61K 31/277* (2006.01)
*A61K 9/00* (2006.01)

(52) U.S. Cl.
CPC ............. *A61K 9/0048* (2013.01); *A61K 31/277* (2013.01)

(58) Field of Classification Search
CPC ............................ C07C 255/00; C07C 317/00
USPC .................................................. 514/519, 520
See application file for complete search history.

(56) References Cited

U.S. PATENT DOCUMENTS

| | | |
|---|---|---|
| 7,923,245 B2 | 4/2011 | Furue et al. |
| 2007/0213396 A1 | 9/2007 | Thielert et al. |
| 2009/0030036 A1 | 1/2009 | Dalton et al. |
| 2010/0226943 A1 | 9/2010 | Brennan et al. |
| 2011/0275583 A1 | 11/2011 | Bretschneider et al. |
| 2013/0252924 A1 | 9/2013 | Penninger et al. |
| 2013/0253054 A1 | 9/2013 | Shah |

FOREIGN PATENT DOCUMENTS

EP   2436729 A1   4/2012

OTHER PUBLICATIONS

Henk P.M. Vijverberg et al., Neurotoxicological Effects and the Mode of Action of Pyrethroid Insectides, Toxicology Rightslinks, 1990, pp. 105-126.
Joost Felius et al., Visual Deprivation and Foveation Characteristics Both Underlie Visual Acuity Deficits in Idiopathic Infantile Nystagmus, The Association for Research in Vision and Ophthalmology, Inc. (IVOS), May 2013, vol. 54, No. 5, pp. 3520-3525.
Li-Ming He et al., Environmental Chemistry, Ecotoxicity and Fate of Lambda-Cyhalothrin, Reviews of Environmental Contamination and Technology, Springer 2008, pp. 71-91 (D.M. Whitacre ed.).

*Primary Examiner* — My-Chau T Tran
(74) *Attorney, Agent, or Firm* — Hudak, Shunk & Farine Co. LPA

(57) ABSTRACT

The present invention relates to the use of a pharmaceutical composition comprising a pyrethroid compound for inhibiting unwanted eye movement and for treating eye movement disorders, such as, but not limited to, nystagmus. The invention is directed to methods for treating unwanted eye movement and eye movement disorders by administering a pharmaceutical composition comprising a pyrethroid compound that is lambda cyhalothrin or an analog thereof, through topical administration of the composition or incorporation of the composition into a contact lens or an ocular device for implantation into the eye. It further provides for pharmaceutical compositions for the treatment of eye movement disorders and methods of preparing them.

13 Claims, 4 Drawing Sheets

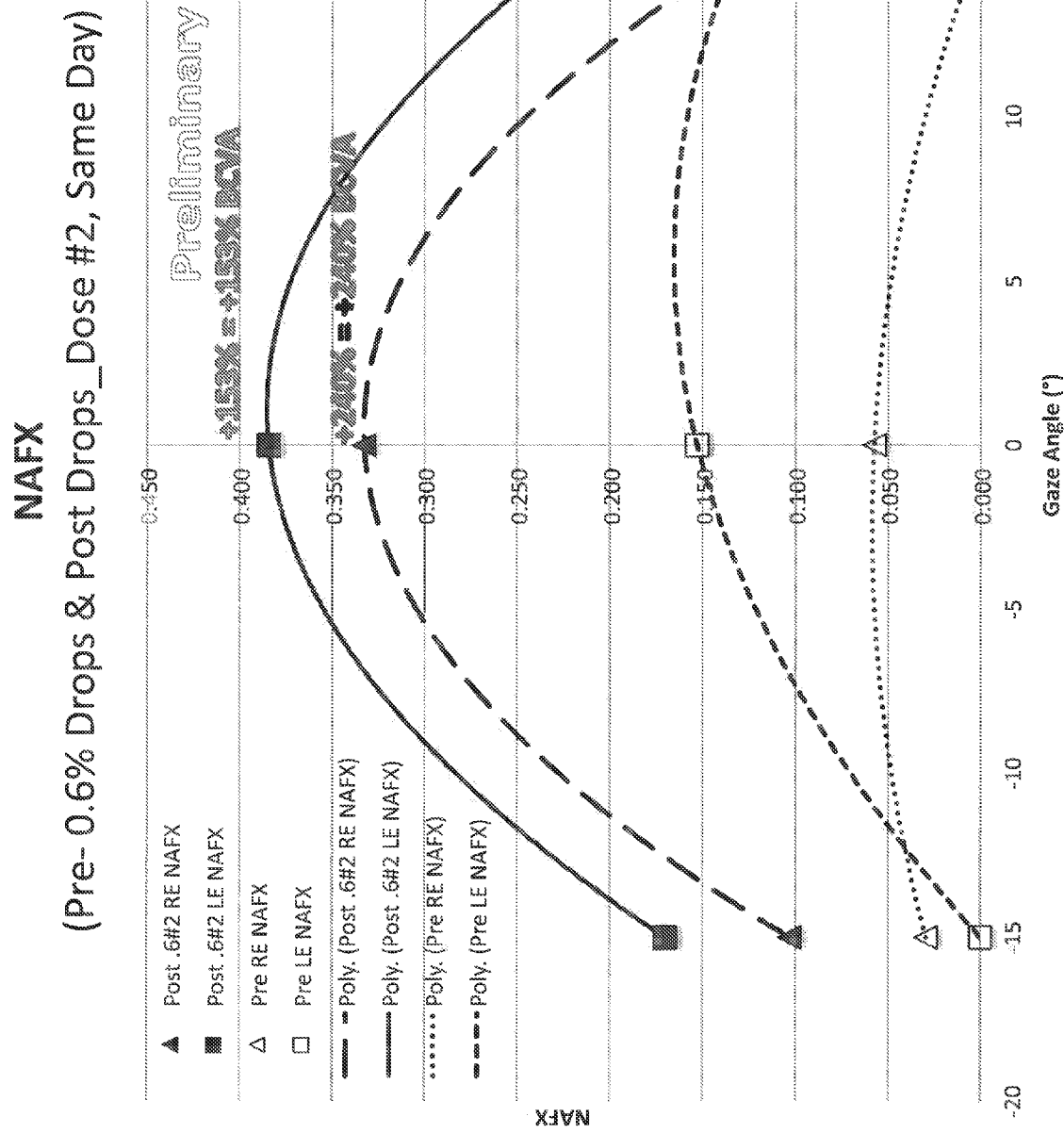

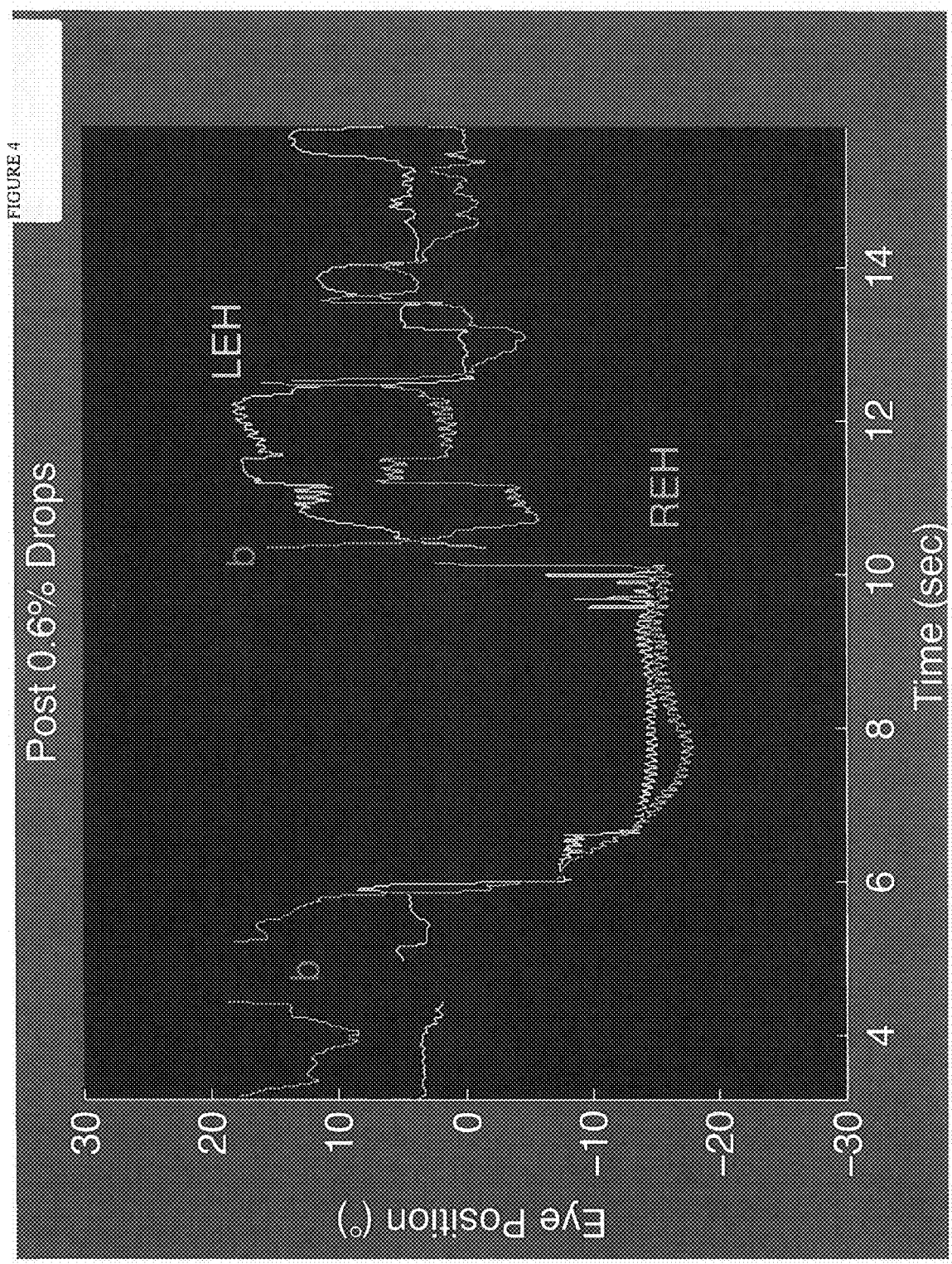

PYRETHROIDS FOR TREATMENT OF OCULAR MOVEMENT DISORDERS

FIELD OF THE INVENTION

The present invention relates to the use of a composition comprising a pyrethroid compound for inhibiting unwanted eye movement and for treating eye movement disorders, such as nystagmus, by topical application of, or implantation of an ocular device containing, the composition. It further provides pharmaceutical compositions for treatment of eye movement disorders and methods for preparing them.

BACKGROUND OF THE INVENTION

Nystagmus comes from the Greek word "nystagmos", which means to nod or drowsiness, and "nystazein" to doze. It is a rhythmic, involuntary oscillation of one or both eyes. Using the information obtained from a complete history, physical examination, and radiographic and eye movement recordings, over forty types of nystagmus can be distinguished. Some forms of nystagmus are physiologic, whereas others are pathologic.

Although nystagmus is typically described by its more easily observable fast (jerk) phase, the salient clinical and pathologic feature is the presence of a slow phase in one or both directions. Thus, clinical descriptions of nystagmus are usually based on the direction of the fast phase and are termed horizontal, vertical, torsional, or any combination of these. The nystagmus may be conjugate or dysconjugate. The nystagmus may be predominantly pendular or jerky, the former referring to equal velocity to-and-fro movement of the eyes, and the latter referring to the eyes moving faster in one direction and slower in the other. Involuntary ocular oscillations containing only fast phases are "saccadic oscillations and intrusions" and not nystagmus. It is well documented that these differences may be difficult, if not impossible, to differentiate clinically and can only be accomplished with eye movement recordings. Recent advances in eye movement recording technology have increased its application in infants and children who have clinical disturbances of the ocular motor system.

Infantile nystagmus syndrome (INS) is an ocular motor disorder of unknown etiology, which presents at birth or early infancy and is clinically characterized by involuntary oscillations of the eyes. INS is defined according to the National Eye Institute collaborative Classification of Eye Movement Abnormalities and Strabismus (CEMAS). Estimations of incidence of INS vary from 1 in 500 to 1 in 6,000. Clinical characteristics include: increased intensity with fixation and decreased with sleep or inattention; variable intensity in some position of gaze (a null position); changing direction in different positions of gaze (about a neutral position); decreased intensity (damping) with convergence; anomalous head posturing; strabismus; and the increased incidence of significant refractive errors. INS can occur in association with congenital or acquired defects in the visual sensory system (e.g., albinism, achromatopsia, and congenital cataracts).

Nystagmus can cause significant impairment in vision. Visual symptoms are very common and are inversely proportional to the frequency (and speed) of the oscillation in the eye. Visual sensitivity for both pattern and movement detection is reduced because of these eye movements. Images spend little time in the foveal area, and image movement, often in excess of 80 degrees/second causes blur, oscillopsia, diplopia, and vertigo. These symptoms begin at retinal slip velocities of greater than 4 degrees/second. Abolishing or reducing the nystagmus frequency ameliorates these symptoms.

Ideally, the treatment of nystagmus would be directed against the pathophysiological brain mechanism responsible for the ocular oscillation. Alternative secondary ameliorative therapies treat the eyes directly, and include prism glasses, contact lenses, occlusion of one eye, botulinum toxin, anesthetic injections, and eye muscle surgery.

INS and adult nystagmus may respond to drug treatment. Some patients benefit from gabapentin, scopolamine, clonazepam, or valproate. All of these drugs have limited usefulness due to a significant number of systemic side effects.

Multiple examples of level II and II based-medical evidence suggest that eye muscle surgery improves nystagmus and visual function in patients with INS or adult nystagmus. Variables reported pre- and post-operatively in patients with INS include: optotype and gaze dependent acuity, contrast sensitivity, motion detection, null zone characteristics, visual recognition time, subjective visual function and electrophysiological characteristics. Patients from multiple studies, who had their null zone optotype best-corrected binocular vision tested within 1 week and 4 to 6 weeks after eye muscle surgery (INS grouped mean data), showed a significant improvement. Overall, seventy-five percent improved 1-3 lines and fifteen percent improved 3 lines or greater.

Eye movement recordings also show that surgical intervention increases the prevalence of favorable nystagmus waveforms. However, even if the nystagmus is completely eliminated, the integrity of the afferent system (optic nerve, retina, brain disease) and the age-related timing of surgery limit the acuity potential in any one patient with INS.

As a result of eye muscle surgery improving their beat-to-beat nystagmus, patients receive more useful vision per unit time and as a function of gaze, recognize objects faster, have less head movement, better motion, and contrast sensitivity, thus "function" better. The common clinical perception is that eye muscle surgery only serves to centralize the INS null position. In fact, what happens is a broadening and deepening of the null zone. Data accumulated over the last 30 years shows that many afferent and efferent visual system measures improve as a result of eye muscle surgery on INS patients, regardless of the indication (eccentric null, vergence damping, strabismus or nystagmus alone), suggesting that neurovisual changes take place as a result of the surgical procedure itself, unrelated to moving or removing some of the extra ocular muscle. The current hypothesis is that surgical interference with peripheral extraocular muscle/tendon, "enthesial" proprioceptive nerve endings influence central ocular motor pathways, resulting in an improved INS oscillation.

Electrophysiological analysis using precise eye movement recordings have provided a new basis for eye movement abnormality classification, etiology, and treatment. These electrophysiological investigations have had a significant impact on eye movement systems research in much the same way as electrocardiography did on the study of cardiac rhythms. Eye movement recording methodology is most commonly used as a research tool by neurologists, neurophysiologists, psychophysicists, psychologists/psychiatrists, ophthalmologists, and optometrists. Practical applications of eye movement recording technology in clinical medicine include diagnosis/differentiation of eye movement disorders and utility as an "outcome measure" in clinical research. Eye movement recordings, by convention, display data during continuous periods of time. Position and velocity traces are clearly marked with up being rightward or upward eye movements and down being leftward or downward eye movements.

Multiple studies have used measures obtained from eye movement recordings to evaluate varied treatment effects on patients with nystagmus. For example, Kim et al., Jain et al., DePalo et al., Bandini et al., Stahl et al., Young et al., Leigh et al., and Hertle et al. all used frequency measures obtained from eye movement recordings to evaluate varied treatment effects on patients with nystagmus. In those studies where therapy decreased the patient's symptoms and signs, eye movement recordings showed an improvement in the nystagmus.

It has been discovered that certain pyrethroid compounds, when administered, intraocular, through topical administration or implantation of an ocular device or contact lens containing the pyrethroid, have a significant impact in improving nystagmus and the visual abnormalities associated therewith, without the attendant disadvantages of medication side effects or invasive surgery. The pyrethroid compounds are formulated in a topical ophthalmic delivery system, such as a solution, suspension, ointment or gel, or incorporated into an ocular device, such as an ocular implant, reservoir or contact lens.

Pyrethroids are a group of man-made (synthetic) pesticides designed to resemble the natural pesticide pyrethrum, which is produced by chrysanthemum flowers. Pyrethroids disrupt the normal functioning of the nervous system in an organism or animal, including human, by prolonging the deactivation of voltage-gated sodium channels, which results in prolonged excitation of nerve fibers.

Synthetic pyrethroids containing an alpha-cyano group (such as lambda-cyhalothrin, the active ingredient in Hot Shot® Home Insect Control (Spectrum Brands) and Warrior IIR crop protection pesticide (Syngenta)) are more potent in eliciting neurotoxic effects, in comparison to pyrethroids that do not contain an alpha-cyano group.

While synthetic pyrethroids have a higher level of selectivity and toxicity for the insect nervous system, local effects on human skin resulting in paresthesias can occur in association with overexposure. Paresthesias are considered a local effect resulting from cutaneous overexposure to certain synthetic pyrethroids, in contrast to an effect mediated through the central nervous system.

Even so, systemic toxicity is uncommon in humans, as the dermal absorption of these chemicals appears to be minimal. Most cases of systemic poisoning and central nervous system effects from synthetic pyrethroids have been reported in association with occupational overexposure or from intentional ingestion. Field studies of agricultural workers with cutaneous exposure to synthetic pyrethroids have reported that when paresthesias occur, the abnormal sensations usually develop several hours after the time of contact. The paresthesia has been described as ranging from a mild itch to a stinging sensation, with progression to numbness in some cases. These paresthesias can be exacerbated by direct exposure to sunlight and upon contact with water. The duration of symptoms varies, ranging from several hours to approximately 24 hours. In most cases, there are no physical abnormalities (such as erythema, edema, or vesiculation) observed in areas of affected skin.

In a study that investigated abnormalities in neurological signs and electrophysiological findings among individuals who had experienced paresthesias from contact exposure to synthetic pyrethroids, no significant differences were observed in comparison to unexposed (control) subjects. Experimental studies and anecdotal reports have suggested that topical Vitamin E (alpha-tocopherol) can reduce the effect of paresthesias through mechanisms that are not well understood.

The warning label for lambda cyhalothrin-containing insecticides states that it is potentially fatal if swallowed, and that it causes "moderate eye irritation." If the product contacts the eyes, the label recommends immediate rinsing followed by seeking the advice of a poison control center or physician. When handling the product, it indicates that handlers must wear eye protection.

It is an object of the invention to provide an ophthalmic composition comprising a pyrethroid compound useful in the treatment of eye movement disorders characterized by unwanted eye movements, such as nystagmus.

It is a further object of the invention to provide a method for the treatment of nystagmus or other conditions involving unwanted eye movements, which provides for significant and prolonged reduction of unwanted eye movements with little or no toxic local or systemic side effects.

It is yet another object of the invention to provide for pharmaceutical compositions comprising an effective amount of a pyrethroid compound, which may be administered topically in the eye or incorporated into an ocular implant, including but not limited to a reservoir, matrix, contact lens or other solid implantable device.

Still other objects of the invention will be evident from the disclosure herein.

SUMMARY OF THE INVENTION

The present invention relates to the use of a pyrethroid compound for inhibiting unwanted eye movement and for treating eye movement disorders, such as but not limited to nystagmus.

In a first non-limiting embodiment, the present invention provides for a method of decreasing unwanted eye movement in a human subject comprising administering, to the subject, an effective amount of a pyrethroid compound. In particular non-limiting embodiments, the unwanted eye movement is nystagmus. In particular non-limiting embodiments, the pyrethroid compound is lambda-cyhalothrin or an analog thereof.

In a second non-limiting embodiment, the present invention provides for a method of treating an eye movement disorder in a human subject comprising administering, to the subject, an effective amount of a pyrethroid compound. In particular non-limiting embodiments, the eye movement disorder is characterized by involuntary movements selected from the group consisting of nystagmus, saccades, and a combination thereof. In particular non-limiting embodiments, the pyrethroid compound is lambda-cyhalothrin or an analog thereof.

In a third non-limiting embodiment, the present invention provides for a method of treating a defect in visual acuity associated with an eye movement disorder in a human subject comprising administering, to the subject, an effective amount of a pyrethroid compound. In particular non-limiting embodiments, the pyrethroid compound is lambda-cyhalothrin or an analog thereof.

In a fourth non-limiting embodiment, the present invention provides for a method of treating vertigo in a human subject comprising administering, to the subject, an effective amount of a pyrethroid compound. In particular non-limiting embodiments, the pyrethroid compound is lambda-cyhalothrin or an analog thereof.

In a fifth non-limiting embodiment, the present invention provides for a pharmaceutical composition comprising an effective amount of a pyrethroid compound in a suitable carrier or ocular device. In particular non-limiting embodiments, the pyrethroid compound is lambda-cyhalothrin or an analog thereof.

BRIEF DESCRIPTION OF THE DRAWINGS

FIG. 3 shows nystagmus acuity function (NAFX) data collected directly from the canine while looking straight ahead (0) and to the left (−15) and right (+15) 15 degrees using a video eye movement system.

FIG. 4 is an actual eye movement recording display of the canine's eye position after the topical administration of two doses of 0.6% concentration pyrethroid composition as an eye drop.

DETAILED DESCRIPTION OF THE INVENTION

Figure 1:
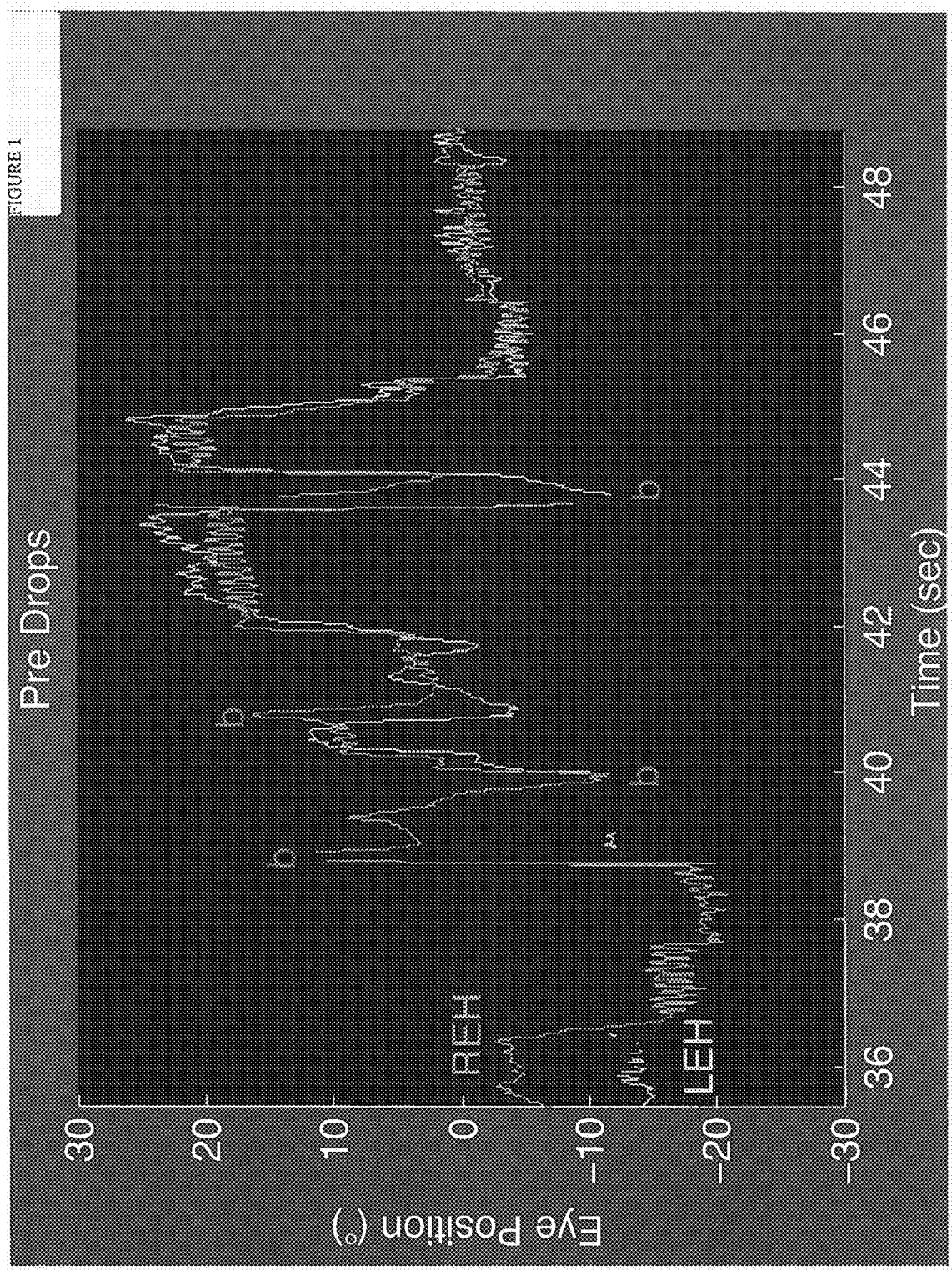
FIG. 1 shows actual eye movement recording display of the canine's eye position at baseline prior to the administration of any eye drop medication.

Pyrethroid compounds useful in the non-limiting embodiments of the invention include any pyrethroid compound known in the art, including but not limited to, lambda-cyhalothrin (Hot Shot® Home Insect Control (Spectrum Brands), Warrior HR® (Syngenta)), cypermethrin (Deep Reach™ Fogger (S. C. Johnson)), deltamethrin (Termite & Carpenter Ant Dust/Killer (Bonide)), allethrin (Ortho® Home Defense Flying Insect (The Scotts Company, LLC)), Raid® House and Garden (S. C. Johnson)), bifenthrin (Ortho® Bug B Gon Max (The Scotts Company, LLC)), cyfluthrin (TEMPO), prallethrin (Ortho® Pro-Select™ Roach, Ant & Spider Killer (The Scotts Company, LLC)), permethrin, resmethrin (Bonide), sumithrin (Ortho® Pro-Select™ Hornet & Wasp Killer (The Scotts Company, LLC)), tetratmethrin and tralomethrin (Wasp and Hornet Killer III (Spartan Chemical Co.)). Preferably, but not by way of limitation, a pyrethroid for use according to the invention contains an alpha-cyano group.

In particular non-limiting embodiments, the present invention utilizes lambda-cyhalothrin, $C_{23}H_{19}ClF_3NO_3$, (R)-cyano(3-phenoxyphenyl)methyl(1S,3S)-rel-3-[(1Z)-2-chloro-3,3,3-trifluoro-1-propenyl]-2,2-dimethylcyclopropanecarboxylate, having Formula 1, below:

Formula 1

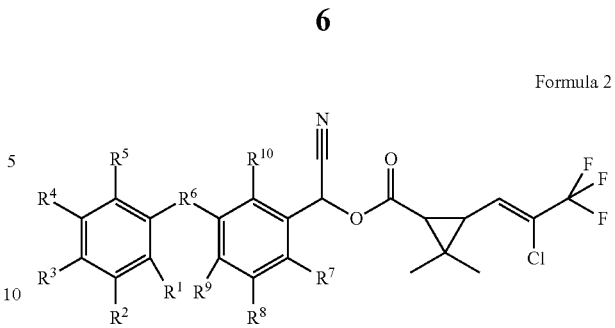

In other non-limiting embodiments, the present invention utilizes a lambda-cyhalothrin analog having Formula 2, below:

Formula 2

Where $R^1$-$R^5$ and $R^7$-$R^{10}$ each may be the same or different (relative to any other of $R^1$-$R^4$ and $R^1$-$R^{10}$) and may be hydrogen (H), alkyl (e.g. $C_1$-$C_4$ alkyl, methyl, ethyl), alkoxy (e.g. $C_1$-$C_4$ alkoxy, methoxy, ethoxy), hydroxyl, or halogen (e.g. F, Cl, Br, I), and any one of $R^1$-$R^5$ and $R^7$-$R^{10}$ is preferably H; and Where $R^6$ may be oxygen (O), nitrogen (N), or alkyl (e.g. $C_1$-$C_4$ alkyl) and preferably is O.

In other non-limiting embodiments, the present invention utilizes a lambda-cyhalothrin analog having Formula 3, below:

Formula 3

Where $R^{11}$ may be O or N or alkyl (e.g. $C_1$-$C_4$ alkyl) and preferably is O;

Where $R^{12}$ may be C=) (ketone) or C—OH or unbranched or branched alkyl (e.g. $C_1$-$C_4$ alkyl) or C—$SO_2$ or C—SH (sulfhydryl) and preferably is C=O; and Where $R^{13}$ is substituted or unsubstituted alkyl (e.g. $C_1$-$C_4$ alkyl) or substituted or unsubstituted $CH_2$—NH—$CH_2$ or a pyrrole ring; wherein one or more substituent, if present, may be alkyl (e.g. $C_1$-$C_4$ alkyl, methyl, or ethyl), alkoxy (e.g. $C_1$-$C_4$ alkoxy, methoxy, ethoxy), hydroxyl, or halogen (e.g. F, Cl, Br, I); and preferably is $C(CH_3)_2$.

In other non-limiting embodiments, the present invention utilizes a lambda-cyhalothrin analog having Formula 4, below:

Formula 4

Where $R^{14}$-$R^{20}$ each may be the same or different (relative to any other of $R^{14}$-$R^{20}$) and may be hydrogen (H), alkyl (e.g. $C_1$-$C_4$ alkyl, methyl, ethyl), alkoxy (e.g. $C_1$-$C_4$ alkoxy, methoxy, ethoxy), hydroxyl, or halogen (e.g. F, Cl, Br, I), and $R^{14}$ preferably is Cl, any one of $R^{15}$-$R^{17}$ preferably is F, and any one of $R^{19}$ and $R^{20}$ preferably is alkyl (e.g. $C_1$-$C_4$ alkyl) and more preferably is methyl.

In other non-limiting embodiments, the present invention utilizes a lambda-cyhalothrin analog having Formula 5, below:

Formula 5

Where $R^{18}$ may be a substituted or unsubstituted aryl, a substituted or unsubstituted naphthyl, a substituted or unsubstituted purine, a substituted or unsubstituted pyrimidine, a substituted or unsubstituted pyrrole, a substituted or unsubstituted biphenyl, a substituted or unsubstituted cyclic alkyl, a substituted or unsubstituted bicyclic alkyl, or a substituted or unsubstituted bicyclic compound where two aromatic rings, preferably two phenyl rings, are joined via an alkyl (e.g. $C_1$-$C_4$ alkyl, methyl, ethyl), O or N (preferably phenoxyphenyl); wherein one or more substituent, if present, may be alkyl (e.g. $C_1$-$C_4$ alkyl, methyl, ethyl), alkoxy (e.g. $C_1$-$C_4$ alkoxy, methoxy, ethoxy), hydroxyl, or halogen (e.g. F, Cl, Br, I), and preferably is an unsubstituted phenoxyphenyl joined to the rest of the molecule at the 3 position; and Where $R^{14}$-$R^{20}$ are as set forth above.

In other non-limiting embodiments, the present invention utilizes a lambda-cyhalothrin analog having Formula 6, below:

Formula 6

Where $R^{18}$ and $R^{14}$-$R^{20}$ are as set forth above.

In other non-limiting embodiments, the present invention utilizes a lambda-cyhalothrin analog having Formula 7, below:

Formula 7

Where $R^1$-$R^{17}$ are as set forth above.

In non-limiting embodiments, the present invention provides for a pharmaceutical compound or device comprising a pyrethroid compound according to Formula 1, 2, 3, 4, 5, 6, and/or 7, and methods of use thereof.

The present invention may be used to treat any movement disorder where inhibition of eye movement is desirable. A substantial proportion of such disorders are eye movement disorders associated with involuntary movements, such as nystagmus and saccade. Other eye movement disorders that may be inhibited and/or treated according to the invention include, but are not limited to, saccadic intrusion, saccadic oscillation, and saccadic nystagmus. Non-limiting examples of types of nystagmus include vertical nystagmus, horizontal nystagmus, torsional nystagmus, and seesaw nystagmus. Another non-limiting category of eye movement disorders to which the invention may be applied are characterized by fixation instability.

Specific non-limiting examples of disorders associated with nystagmus or saccadic movements that may be treated according to the invention include infantile nystagmus syndrome; paroxysmal positional benign nystagmus; positional nystagmus of central nervous system origin; Meniere's disease; pseudotumor cerebri; benign intracranial hypertension; vertebrobasilar migraine syndrome; cerebellum degeneration, cortical par, multiple sclerosis; optic atrophy, idiopathic; optic atrophy, primary; acro-osteolysis/Hadju-Cheney Syndrome; cerebellar degeneration, subacute; Gerstmann-Straussler-Scheinker (GSS) Disease and intoxications or side effects or anti-seizure and/or neuropsychiatric medications.

Symptoms of the foregoing disorders that may be treated according to the invention include, but are not limited to, blurred vision, poor visual acuity, oscillopsia, double vision, vertigo, nausea, poor contrast sensitivity, motion processing, visual recognition time, gaze dependent visual acuity and head posturing and secondary neck and spine problems due to the oscillation.

The present invention may be used to inhibit the activity of the neuromuscular apparatus of the distal portion of the extraocular muscle at its insertion of the globe. Without being bound by any particular theory, it is believed that such inhibition, in cases where the involuntary eye movement originates in the brain, secondarily affects regulatory centers in the brain, modulating feedback loops between the nerves and extraocular muscles and brain centers involved in controlling ocular motor function.

The present invention provides for a pharmaceutical composition comprising an effective amount of a pyrethroid compound dispersed in a suitable carrier, such as a solution, suspension, emulsion, gel or ointment for topical application or injection into the eye; or incorporated into an ocular device, including but not limited to an ocular implant, reservoir, matrix, contact lens or other solid implantable device. In a preferred embodiment, the pharmaceutical composition is an eye drop or ointment. It is desirable that the pharmaceutical compositions be sterile or sterilizable.

In a preferred embodiment, the composition comprises a pyrethroid compound that is lambda-cyhalothrin or an analog thereof. Suitable pyrethroid compounds and lambda-cyhalothrin analogs are described above in Formula 1-7.

For purposes of the invention, an "effective amount" means and includes an amount that reduces or eliminates an unwanted eye movement and/or decreases the manifestation and/or symptom of an eye movement disorder. As one non-limiting example, where the unwanted eye movement is nystagmus, an "effective amount" is an amount which is sufficient to reduce or eliminate signs or symptoms of nystagmus. Further, an "effective amount" may be an amount which reduces or eliminates blurred vision, poor visual acuity, double vision, vertigo, oscillopsia, or nausea.

An "effective" concentration of pyrethroid, lambda-cyhalothrin or lambda-cyhalothrin analog, is between about 0.001 to about 5.0 percent (weight pyrethroid/weight composition ("w/w")) or between about 0.001 to about 1.0 percent (w/w)

or between about 0.01 to about 1.0 Percent (w/w). "About" means plus or minus 20 percent.

The pharmaceutical compositions of the present invention may also include various other ingredients, including but not limited to one or more surfactants, tonicity agents, buffers, antimicrobial agents, preservatives, co-solvents, and/or viscosity building agents. Suitable ingredients are known to one skilled in the art of ophthalmic pharmaceuticals and their preparation.

Suitable surfactants include surface-active agents that are traditionally used in ophthalmic or otolaryngological uses, such as polysorbate 80 (TWEEN® 80, ICI America Inc.), tyloxapol, as well as PLURONIC® F-68 (BASF) and other poloxamer surfactants. These latter two surfactants are non-ionic polyalkylene oxide block copolymers useful to improve water solubility and/or miscibility of hydrophobic compounds. The concentration in which any particular surfactant is used may be limited by its potential for neutralization of the bactericidal effects of preservatives (if present), or by levels that may cause irritation. Other useful surfactants and their useful concentrations will be known to one skilled in the art.

Various tonicity agents may be employed to adjust the tonicity of the composition. For example, sodium chloride, potassium chloride, magnesium chloride, calcium chloride, nonionic diols, preferably glycerol, dextrose, and/or mannitol may be added to the composition to approximate physiological tonicity. The amount of tonicity agent desirable may vary, depending on the particular agent to be added. In preferred non-limiting embodiments of the invention, a pharmaceutical composition comprises a tonicity agent in an amount sufficient to cause the final formulation to have an ophthalmically acceptable osmolality (generally about 150-450 mOsm).

The inventive pharmaceutical compositions may comprise an appropriate buffer system (e.g. sodium phosphate, sodium acetate, sodium citrate, sodium borate, or boric acid) to reduce or prevent pH drift under storage conditions. Other appropriate buffers would be known to one skilled in the art. The particular concentration used would vary depending on the agent employed.

In some preparations according to the invention, such as a multidose composition, it is desirable to include a preservative or antimicrobial agent to reduce or prevent microbial contamination. Suitable preservatives include but are not limited to: biguanides, hydrogen peroxide, hydrogen peroxide producers, benzalkonium chloride, chlorobutanol, benzododecinium bromide, methyl paraben, propyl paraben, phenyl ethyl alcohol, edetate disodium, sorbic acid, polyquaternium-1, and/or other preservative or antimicrobial agents known to those skilled in the art to be safe in ophthalmic preparations. In specific non-limiting embodiments, a preservative is present at a concentration between about 0.001 to about 1.0 percent (w/w). Preferably, a single unit dose formulation of the present invention is sterile and does not require a preservative.

A pharmaceutical composition of the invention may optionally further comprise one or more co-solvents and/or viscosity building agent. Suitable agents include but are not limited to: a nonionic water-soluble polymer, an agent that lubricates, "wets," and approximates the consistency of endogenous tears, and/or an agent that aids in natural tear build-up, or otherwise provides temporary relief of dry eye symptoms. Exemplary compounds include, without limitation, monomeric polyols, such as, glycerol, propylene glycol, ethylene glycol; polymeric polyols, such as, polyethylene glycol, hydroxypropylmethyl cellulose (HPMC), carboxy methylcellulose sodium, hydroxypropylcellulose (HPC), dextrans, such as, dextran 70; water soluble proteins, such as gelatin; and vinyl polymers, such as polyvinyl alcohol, polyvinylpyrrolidone, povidone, and carbomers, such as carbomer 934P, carbomer 941, carbomer 940, and carbomer 974P.

A "phospholipid carrier" or "artificial tears" formulation recommended for the treatment of dry eye may be comprised in the pyrethroid-containing pharmaceutical compositions of the invention. Such phospholipid carrier or artificial tears carriers are aqueous formulations which: (i) comprise one or more phospholipid or other compound that lubricates, "wets," and/or approximates the consistency of endogenous tears, aids in natural tear build-up, and/or otherwise provides temporary relief of dry eye symptoms and conditions upon ocular administration; (ii) are substantially clinically safe to use; and (iii) provide the appropriate delivery vehicle for the topical administration of an effective amount of pyrethroid. Non-limiting examples of artificial tears formulations useful as artificial tears carriers include commercial products such as Moisture Eyes™ Lubricant Eye Drops/Artificial Tears, Moisture Eyes™ Liquid Gel lubricant eye drops, Moisture Eyes™ Preservative Free Lubricant Eye Drops/Artificial Tears and Moisture Eyes™ Liquid Gel Preservative Free Lubricant Eye Drops/Artificial Tears (Bausch & Lomb Incorporated, Rochester, N.Y.). Non-limiting examples of phospholipid carrier formulations include those disclosed in U.S. Pat. No. 4,804,539 (Guo et al.), U.S. Pat. No. 4,883,658 (Holly), U.S. Pat. No. 4,914,088 (Glonek), U.S. Pat. No. 5,075,104 (Gressel et al.), U.S. Pat. No. 5,278,151 (Korb et al.), U.S. Pat. No. 5,294,607 (Glonek et al.), U.S. Pat. No. 5,371,108 (Korb et al.), U.S. Pat. No. 5,578,586 (Glonek et al.), the contents of each of which are incorporated by reference herein.

Optionally, other compounds may also be added to the ophthalmic formulations of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers.

The present invention provides for a method of producing a sterile pharmaceutical composition of the invention that is a gel prepared by first preparing a sterile polyacrylate gel and then incorporating an effective amount of a sterile pyrethroid (e.g. lambda-cyhalothrin or an analog thereof) into said gel.

Alternatively, the pyrethroid compound (lambda-cyhalothrin or an analog thereof) may be suspended with a part of a solution, which may contain a sterile tonicity agent, used for the production of a polyacrylate gel, and this suspension is then homogenously mixed in with a separately sterilized polyacrylate gel.

Sterilization may be accomplished using a variety of steps. For example, according to one specific non-limiting embodiment of the present invention, an aqueous polyacrylate suspension is made and then autoclaved under sterile conditions. This acrylate suspension is mixed with a sterile-filtrated solution of preserving agent, isotonicity agent, and chelating agent. After careful and thorough mixing of the starting materials, the addition of sterile-filtrated caustic soda solution initiates gel formation, and the gel is further subjected to agitation until it is homogenous. Meanwhile, a pyrethroid (e.g. lambda-cyhalothrin or an analog thereof) is sterilized, for example by dissolving the pyrethroid in a suitable amount of solvent, for example ethyl acetate, subjecting the solution to sterile filtration, and precipitating the pyrethroid, for example, through the addition of sterile water with an antimicrobial agent under aseptic conditions. The microbially sterile pyrethroid may then be triturated or ground to a powder with about three to ten times that amount of the gel base.

The remaining amount of gel may then be incorporated in the concentrate by thorough mixing. The finished gel preparation is then conventionally decanted or drawn off under sterile conditions.

In an alternative variation of this method, the microbially sterile pyrethroid (e.g. lambda-cyhalothrin or an analog thereof) can be, to a large extent, suspended in a part of the aqueous solution of the tonicity agent. The polyacrylate gel can be made in a conventional manner with the remaining amount of isotonic agent and separately the isotonic suspension of the pyrethroid can be homogenously mixed with the polyacrylate under sterile conditions.

Exemplary ophthalmic solutions are set forth below: however, the invention is not limited as such. The formulations are typical of ophthalmic formulations in terms of carrier and optional components. Other formulations and methods of preparing sterile ophthalmic drug delivery systems are known in the art.

Formulation 1
Ingredient Amount
Phase I
Carbopol® 934P NF (a high molecular weight acrylic acid-based polymer) 0.25 gm.
Purified Water 99.75 gm
Phase II
Propylene Glycol 5.0 gm
Ethylenediamine tetraacetic acid (EDTA) 0.1 mg
Lambda-cyhalothrin "x" gm (where x is an amount that when diluted in the final composition produces an effective therapeutic composition).
Mix five parts of phase II with twenty parts of phase I for more than 15 minutes and adjust pH to 6.2-6.4 using 1 N NaOH.

Formulation 2
Phase I
Carbopol® 934P NF (a high molecular weight acrylic acid-based polymer) 0.25 gm
Purified Water 99.75 gm
Phase II
Propylene Glycol 3.0 gm
Triacetin 7.0 gm
Lambda-cyhalothrin "x" gm (where x is an amount that when diluted in the final composition produces an effective therapeutic composition)
EDTA 0.1 mg
Mix five parts of phase II with twenty parts of phase I for more than 15 minutes and adjust pH to 6.2-6.4 using 1 N NaOH.

Formulation 3
Ingredient Amount
Phase I
Carbopol® 934P NF (a high molecular weight acrylic acid-based polymer) 0.25 gm
Purified Water 99.75 gm
Phase II
Propylene Glycol 7.0 gm
Glycerin 3.0 mg
Lambda-cyhalothrin "x" gm (where x is an amount that when diluted in the final composition produces an effective therapeutic composition)
EDTA 0.1 mg
Benzalkonium chloride (BAK) 0.1-0.2 mg
Mix five parts of phase II with twenty parts of phase I for more than 15 minutes and adjust pH to 6.2-6.4 using 1 N NaOH.

Formulation 4

A gel may be useful in the application of the present compositions. One method of making a gel is set forth below. The production of larger amounts of gel may be necessary to meet commercial demands. For illustration purposes, a gel is produced with water that is suitable for injection purposes (injection grade). To produce 500 gm of polyacrylate gel, 1.220 gm of polyacrylic acid (packaged under the trademark "Carbopol® 980 NF") is carefully suspended, with the aid of an ultrasonic apparatus, in about 700 ml water and autoclaved for 20 minutes at 1210° C. and 2 bar pressure. In 700 ml of sterile injection-grade water is then dissolved 0.050 gm of benzalkonium chloride (BAK), 20.000 gm sorbitol and 0.050 gm of sodium EDTA (X 2H2O), which is then subjected to sterile filtering (Sartorius® Cellulose nitrate filter, order no. 11307-50ACN, 0.2 µm) into a sterile vessel. The sterile-filtered salt solution is then mixed, with strong agitation, into the autoclaved polyacrylate suspension. Sterile water in the amount of 1958.121 gm is then added, and the solution is subjected to further agitation for 5 to 10 minutes. Subsequently, strong sodium hydroxide in the amount of 0.465 gm is dissolved in 40 gm of injection-grade water. This caustic soda is then introduced drop-wise under agitation over a sterile filter (Millex-GS, 0.22 µm, SLGS 025 BS der Fa. Millipore). The mixture is agitated until the formation of a completely homogenous gel.

To make the pharmaceutical composition of the invention, a microbially sterile lambda-cyhalothrin is then slowly and carefully mixed with about 30 to 50 gm of the gel. The gel is subjected to sterile filtration of the solution, and separation with water containing a bactericide under sterile conditions. After the loteprednol etabonate (ALREX®, LOTEMAX®) is dissolved in the given amount of gel to separate the composition. The rest of the gel, in total 495 gm, is carefully incorporated into the initial material. All method steps are carried out under aseptic conditions. The prepared gel is likewise drawn off in tubes under aseptic conditions.

By an alternative method, the microbially sterile lambda-cyhalothrin is suspended in a sterile-filtrated isotonic solution of 700 ml water, 0.050 gm benzalkonium chloride, 20.000 gm sorbitol and 0.50 mg of disodium EDTA. This solution is then, as already described, incorporated, under strong agitation, into the autoclaved polyacrylate suspension.

The present invention further encompasses alternative formulations of pyrethroid-based treatments, such as, for example, a solid matrix, reservoir, or other device for implantation into the eye, or a contact lens. Alternatively, a pyrethroid may be in a form that is encapsulated, for example in a liposome, and then incorporated into a solution or suspension for administration. The invention is not limited by the particular formulations, delivery systems, preparations or methods set forth herein. One skilled in the art of ophthalmic preparations, whether topical or implantable, would understand a variety of formulations, devices and methods for pyrethroid based treatments.

A pyrethroid containing composition of the invention may be administered to the eye by any method known in the art, including, but not limited to, topical instillation or injection of a solution, suspension, emulsion, gel, or ointment; or the insertion or implantation of an ocular device, including but not limited to a reservoir, ocular implant, reservoir, matrix, or contact lens, or other solid implantable device that provides sustained release of the drug into the eye over time.

Administration of the pharmaceutical compositions of the invention may be at least once a day, at least twice a day, at least once a week, at least twice a week, at least once a month, at least twice a month, at least six times a year, at least four times a year, at least twice a year, or at least once a year, and/or up to twice a day, up to three times a day, up to once a week, up to twice a week, up to three times a month, up to six times a year, or up to four times a year, depending on the particular dosage form and/or delivery system utilized. In a specific non-limiting embodiment, where the inventive pharmaceutical composition is administered as eye drops, 1-2 drops of the pharmaceutical composition comprising between about 0.001 to about 5.0 percent (w/w) or between about 0.001 to about 1.0 percent (w/w) or between about 0.01 to about 1.0 percent (w/w) of pyrethroid may be administered to the affected eye at a time. If the composition is administered through an ocular device, designed to release the pyrethroid compound over time, less frequent dosing would be required.

A treatment regimen using a pyrethroid-containing composition of the invention may, in non-limiting embodiments, be combined with a regimen of treatment using another pharmaceutical agent. For example, where the eye movement disorder being treated is nystagmus, treatment with the inventive compositions may be combined with traditional medications, such as gabapentin, scopolamine, clonazepam, and/or valproate.

EXAMPLES

Methodology

Eye movements were recorded using an EyeLink 1000 remote video recording system, with a sampling rate of 500-1000 Hz.

Efficacy was assessed by video-based eye tracking system wherein eye movement recordings of nystagmus and determination of Nystagmus Acuity Function (NAF, NAFX or eNAFX) was calculated from position and velocity data obtained from calibrated eye movement recordings. Techniques used to collect such data include a scleral search coil, non-contact infrared oculography, video pupillography and electroculography.

Nystagmus Acuity Function—NAF is a derived function that predicts the best-corrected visual acuity possible in subjects with nystagmus. NAF is based upon objective measurements of a subject's waveform characteristics during fixation of a small light-emitting diode and combines the foveation time per cycle and the standard deviations of both eye position and velocity during target foveation into a function that is linearly proportional to best-possible visual acuity.

Evaluation of the nystagmus acuity function (NAF, NAFX, eNAFX) is often used to evaluate the quality of the nystagmus cycle and/or quantify the effect of surgical or pharmaceutical intervention on the nystagmus waveform. To produce the NAF, a series of parameters, such as: foveation duration, foveation eye positions, mean velocity of nystagmus slow phase, combination of foveation eye positions and eye velocities, have been used. Dynamic system analysis, fixed point analysis method, and wavelet spectrum have also been used for nystagmus analysis. Among those methods, the one that uses both foveation eye position and eye velocity criteria, which is called expanded nystagmus acuity function (eNAFX), has been well accepted in research fields and is known to one skilled in the art. The eNAFX uses the following formulas to calculate nystagmus acuity function:

$$NAFX = (1 - \sigma_{pv})[1 - e^{-1/\tau}]$$

$$\sigma_{pv} = \sqrt{(SD_p^2 + SD'^2_v)/2}, SD'_v = (p/v)(SD_n)$$

Foveation eye position ($SD_p$) in the second formula plays an important role in scoring the eNAFX. According to the relationship between visual acuity and eccentric distance from the fovea, visual acuity exponentially drops as the location of a visual target becomes more eccentric to the fovea.

The use of the expanded Nystagmus Acuity Function (NAFX) on nystagmus data yields both an accurate measure of foveation quality and a prediction of maximum potential acuity for the patient's waveform. When used with the patient's measured, pre-therapy visual acuity, the NAFX demonstrates the amount of visual acuity loss that is due to sensory abnormalities, demonstrates the amount due to the nystagmus waveform, and estimates the measured post-therapy acuity for all values of improved NAFX and gaze angles measured.

Amplitude—The amplitude of nystagmus was measured directly from calibrated eye movement recordings in degrees.

Safety was evaluated by: Ocular signs and symptoms, conjunctival erythema or chemosis, eye pain, photophobia, corneal edema, intraocular inflammation, lid swelling and erythema, intraocular pressure changes, lens, and retinal and retinal vessel changes. Systemic signs and symptoms evaluated were vital signs, venous blood samples, and liver and renal function tests. No toxic effects were observed.

Materials: The following materials were used in the examples:

Lambda-cyhalothrin (LC)

Dimethyl sulfoxide (DMSO)

Propylene glycol (PG)

Balanced Salt Solution (BSS)

Preparations: The desired composition was DMSO 4.0%, PG 3.0% and LC 10 mg/ml. (1% (by weight)), based upon the total composition. The preparation of 2.5 ml of the desired composition is shown in Table 1.

A vehicle was prepared for use as a subsequent dilution (serial dilutions of the initial LC strength), by mixing 4.65 ml of BSS, 0.2 ml of DMSO, and 0.15 ml of PG, to yield a diluent vehicle comprising 4.0% DMSO and 3.0% PG, based upon the total weight of the composition. A total of 5 ml was prepared.

The initial base LC formulation according to the invention is set forth in Table 1 below. A maximum concentration of 1.0% (by weight) LC was prepared.

TABLE 1

| COMPONENT/AMOUNT | PREPARATION STEP |
| --- | --- |
| LC 25 mg. | Added to DMSO with mixing. |
| DMSO 0.1 ml | |
| PG 0.075 ml | Mixed with LC/DMSO Mixture |
| BSS 2.325 ml | Slowly added to 0.175 ml LC/DMSO/PG mixture |
| Total 2.5 ml | Final Concentration 1.0% LC, 4.0% DMSO, 3.0% PG |

Methodology: Inventive compositions were prepared by simple mixing.

Progressive dilutions of the composition set forth in Table 1 are shown in Table 2, below, starting with the original 2.5 ml volume preparation of Table 1. These subsequent dilutions were used in the canine experiments set forth below.

TABLE 2

| Vol. remaining of previous % (ml) | Diluent Vehicle to add (ml) | Total Volume (ml) | Vol. removed to dropper (ml) | % LC |
|---|---|---|---|---|
| — | — | 2.500 (starting volume) | 0.250 | 1.0% |
| 2.250 | 0.250 | 2.500 | 0.278 | 0.9% |
| 2.220 | 0.278 | 2.500 | 0.313 | 0.8% |
| 2.188 | 0.313 | 2.500 | 0.357 | 0.7% |
| 2.143 | 0.357 | 2.500 | 0.417 | 0.6% |
| 2.083 | 0.417 | 2.500 | 0.500 | 0.5% |
| 2.000 | 0.500 | 2.500 | 0.625 | 0.4% |
| 1.875 | 0.625 | 2.500 | 0.833 | 0.3% |
| 1.667 | 0.833 | 2.500 | 2.500 | 0.01% |

Example 1

A pyrethroid formulation was prepared, as above, using LC in amounts of 0.6% w/w, based on the weight of the LC to the total weight of the composition. The formulation was administered to canine subjects. Canine subjects have similar anatomical and physiological ophthalmic characteristics and, consequently, are excellent surrogates to assess the results of the use of the inventive compositions on humans. The results after two doses of the formulation showed significant improvement of nystagmus as shown in the accompanying figures.

FIG. 1, Eye Position-Pre Drops shows an actual eye movement recording display of the canine's eye position at baseline prior to the administration of any eye drop medication. As the canine looks to the right and left, a high frequency (9~11) Hz pendular oscillation is present. (The "y" axis shows degrees of eye movement to the right (+) and left (−) from center. The "x" axis shows time in seconds. REH=right eye horizontal; LEH=left eye horizontal; b=blinks. Upward movements on the graph are rightward eye movements, and downward movements on the graph are leftward movements.)

Figure 2:
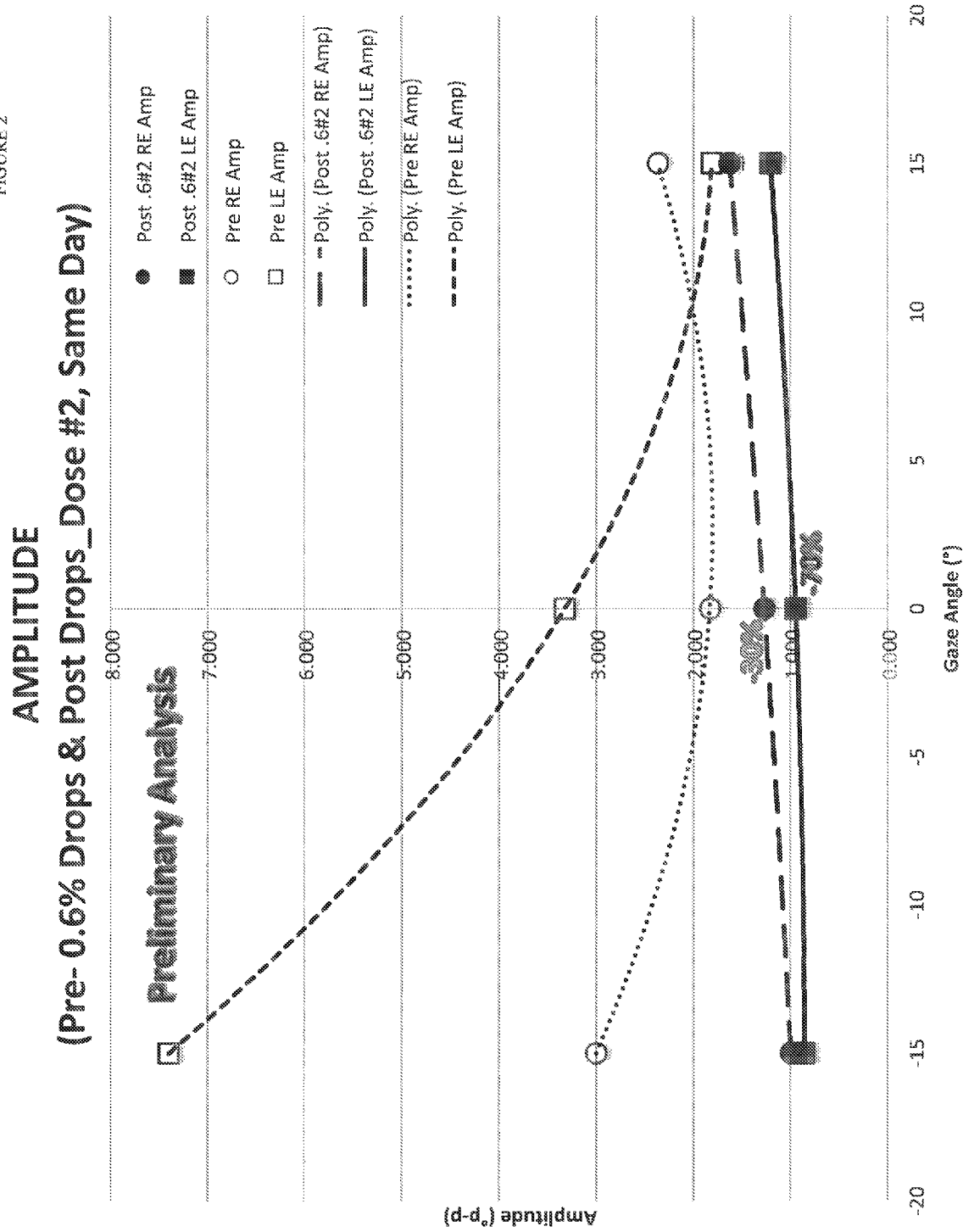
FIG. 2 shows nystagmus amplitude data collected directly from the canine while looking straight ahead (0) and to the left (−15) and right (+15) 15 degrees using a video eye movement system, both pre- and post-administration of the pyrethroid composition.

FIG. 2, Amplitude (Pre-0.6% Drops & Post Drops_Dose #2, Same Day) shows nystagmus amplitude data collected directly from the canine while looking straight ahead (0) and to the left (−15) and right (+15) 15 degrees using a video eye movement system. The data displayed show both baselines, prior to the administration and after two doses of 0.6% LC drops. The dotted and solid lines represent a polynomial analysis connecting the data from the three collected points. The data clearly demonstrates a significant reduction (30%-70%) in nystagmus amplitude across gaze after administration of the 0.6% topical solution of LCL. (The "y" axis shows average amplitude of nystagmus in degrees, and the "x" axis shows degrees of eye movement in the orbit from straight ahead [0 degrees] and between right and left 15 degrees. Pre=prior to drop administration; Post=after drop administration; #2=second dose of the day; RE=right eye; LE=left eye; Amp=amplitude in degrees; poly=polynomial fit obtained from collected data in 3 positions of gaze.

FIG. 3 NAFX (Pre-0.6% Drops & Post Drops_Dose #2, Same Day) shows nystagmus acuity function (NAFX) data collected directly from the canine while looking straight ahead (0) and to the left (−15) and right (+15) 15 degrees using a video eye movement system. The data displayed show both baselines, prior to the administration and after two doses of 0.6% LC drops. The dotted and solid lines represent a polynomial analysis connecting the data from the three collected points. The data clearly demonstrates a significant improvement (153%-240%) in NAFX across gaze after administration of the 0.6% topical solution of LC. (The "y" axis shows average NAFX (from 0, worst to 1, best), and the "x" axis shows degrees of eye movement in the orbit from straight ahead [0 degrees] and between right and left 15 degrees. +BCVA=predicted best corrected visual acuity; Pre=prior to drop administration; Post=after drop administration; #2=second dose of the day; RE=right eye; LE=left eye; NAFX=nystagmus acuity function; poly=polynomial fit obtained from collected data in 3 positions of gaze.

FIG. 4, Eye Position-Post 0.6% Drops shows an actual eye movement recording display of the canine's eye position after the administration of two doses of 0.6% topical LC eye drop medication. As the canine looks to the right and left, the high frequency (9-11) Hz pendular oscillation has less amplitude as compared to the Pre Drop eye movement recording of FIG. 1 and is only present only in extreme gaze. (The "y" axis shows degrees of eye movement to the right (+) and left (−) from center. The "x" axis shows time in seconds. REH=right eye horizontal; LEH=left eye horizontal; b=blinks. Upward movements on the graph are rightward eye movements and downward movements on the graph are leftward movements.)

While in accordance with the Patent Statutes, the best mode and preferred embodiments have been set forth, the scope of the invention is not limited thereto, but rather by the scope of the attached claims.

What is claimed is:

1. A method of treating an eye movement disorder in a human subject comprising a step of: administering a composition comprising an effective amount of a pyrethroid compound into the eye, by topical administration, injection or implantation of an ocular device containing the composition.

2. The method of claim 1 wherein the eye movement disorder is characterized by involuntary movements and is nystagmus, saccades, or a combination thereof.

3. The method of claim 1 wherein the pyrethroid compound is lambda-cyhalothrin.

4. A method of treating a defect in visual acuity associated with an eye movement disorder in a human subject comprising the step of: administering a composition comprising an effective amount of a pyrethroid compound into the eye, by topical administration, injection or implantation of an ocular device containing the composition.

5. The method of claim 4 wherein the pyrethroid compound is lambda-cyhalothrin.

6. A method of treating vertigo in a human subject comprising the step of: administering a composition comprising an effective amount of a pyrethroid compound into the eye, by topical administration, injection or implantation of an ocular device containing the composition.

7. The method of claim 6, wherein the pyrethroid compound is lambda-cyhalothrin.

8. An ophthalmic pharmaceutical composition comprising a pyrethroid compound that is lambda-cyhalothrin present in an amount effective for treating an eye movement disorder or a defect in visual acuity associated therewith or vertigo in a human subject, wherein the compound is dispersed in a suitable carrier.

9. The composition of claim 8, wherein the eye movement disorder is nystagmus, saccades, or a combination thereof.

10. The composition of claim 8, wherein the carrier is an ophthalmic solution, suspension, get emulsion or ointment suitable for topical administration in the eye.

11. The composition of claim 8, wherein the carrier is a solution, suspension, gel, emulsion or ointment suitable for injection into the eye.

12. The composition of claim 8, wherein the carrier is an ocular device in which a solution, suspension, emulsion, gel or ointment containing the composition has been incorporated and which is suitable for insertion or implantation into the eye.

13. The composition of claim 12, wherein the ocular device is a solid matrix, reservoir, implant, contact lens or other solid implantable device.

\* \* \* \* \*